United States Patent

Peyman et al.

[11] Patent Number: 5,817,825
[45] Date of Patent: Oct. 6, 1998

[54] PROCESS FOR THE PREPARATION OF 1-HYDROXY-2-PYRIDONES

[75] Inventors: Anuschirwan Peyman, Kelkheim; Dieter Bernd Reuschling, Butzbach; Adolf Heinz Linkies, Frankfurt, all of Germany

[73] Assignee: Hoechst Aktiengesellschaft, Frankfurt am Main, Germany

[21] Appl. No.: 545,041

[22] Filed: Oct. 12, 1995

[30] Foreign Application Priority Data

Nov. 2, 1994 [DE] Germany .......................... 44 39 029.7
May 16, 1995 [DE] Germany ........................ 195 17 891.2

[51] Int. Cl.$^6$ ........................ C07D 211/72; C07D 213/64
[52] U.S. Cl. ........................ 546/290; 546/301; 546/302; 546/303
[58] Field of Search .................................... 546/290, 301, 546/302, 303

[56] References Cited

U.S. PATENT DOCUMENTS 3,972,888  8/1976  Lohaus et al. .
4,797,409  1/1989  Lohaus et al. ........................... 514/345
4,916,228  4/1990  Reuschling et al. .................... 546/290

FOREIGN PATENT DOCUMENTS 2177963  3/1973  France .
2214608  10/1973  Germany .
3626210  10/1987  Germany .

*Primary Examiner*—Alan L. Rotman
*Assistant Examiner*—Garth M. Dahlen
*Attorney, Agent, or Firm*—Finnegan, Henderson, Farabow, Garrett & Dunner, L.L.P.

[57] ABSTRACT

A process for the preparation of 1-hydroxy-2-pyridones is described in which a pyrone is reacted with a hydroxylammonium salt in the presence of basic compounds, solvents and organic acids or salts thereof.

17 Claims, No Drawings

PROCESS FOR THE PREPARATION OF 1-HYDROXY-2-PYRIDONES

DESCRIPTION

1-Hydroxy-2-pyridones are prepared by the process described in DE 2 214 608 by reaction of the corresponding 2-pyrones (formula II) with hydroxylamine or one of its salts in the presence of an—optionally substituted—aminopyridine or imidazole. The aminopyridine or imidazole is advantageously employed here in at least the equimolar amount with respect to the hydroxylammonium salt. Temperatures between 50° C. and 120° C. are stated as the temperature range. During the reaction, the ring oxygen atom of the 2-pyrone is replaced by the N—OH group. The yields are between 60% and 70% of theory, based on the 2-pyrone employed. This process has the disadvantage that considerable amounts of the relatively valuable and expensive aminopyridines and/or imidazoles are used which, because of their considerable value and also for environmental protection reasons, must be recovered again. Furthermore, the process is very time-consuming.

1-Hydroxy-2-pyridones are prepared by the process described in DE 3 626 210 by reaction of the corresponding 2-pyrones with hydroxylamine or a hydroxylammonium salt in the presence of basic compounds, such as alkali metal carbonate or bicarbonate, at temperatures between 50° C. and 120° C., the alkali metal carbonate advantageously being employed here in at least the equimolar amount with respect to the hydroxylammonium salt. The increased profitability and the low environmental pollution are the advantages of this process compared with that described in DE 2 214 608. The lower yields compared with DE 2 214 608, which are between 50% and 60% of theory, based on the 2-pyrone employed, are a disadvantage of the process described in DE 3 626 210.

It has now been found that the yield of 1-hydroxy-2-pyridones in the process described in DE 36 26 210 can be increased by addition of organic acids or a salt thereof.

The invention relates to a process for the preparation of 1-hydroxy-2-pyridones of the formula I

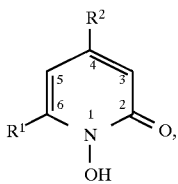

by reaction of a pyrone of the formula II

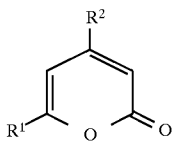

with a hydroxylammonium salt in the presence of basic compounds and solvents, which comprises carrying out the reaction in the presence of an organic acid or a salt thereof and employing as the basic compounds an alkali metal carbonate and/or alkali metal bicarbonate in an amount of 0.8 to 5 equivalents with respect to the hydroxylammonium salt, the radicals $R^1$ and $R^2$ in the formulae I and II having the following meanings:

$R^1$ is a branched or unbranched alkyl having 1 to 17 carbon atoms, preferably 1 to 12 carbon atoms, in particular 1 to 10 carbon atoms, a branched or unbranched alkenyl having 2 to 17 carbon atoms, a cycloalkyl having 3 to 8 carbon atoms in the ring, preferably 6 carbon atoms in the ring; the cycloalkyl radical mentioned being unsubstituted or substituted by 1 to 3 alkyl radicals each having 1 to 3 carbon atoms, a phenyl, phenyloxy-$(C_1-C_4)$alkyl or phenyl-$(C_1-C_4)$alkyl radical which is unsubstituted or substituted in the aromatic nucleus by 1 to 3 $(C_1-C_6)$alkyl, benzyl, $(C_1-C_6)$alkoxy, phenoxy or halogen radicals, it also being possible for the benzyl or phenoxy group present as a substituent to be substituted in the same manner, and the cycloalkyl, phenyl, phenyloxy-$(C_1-C_4)$alkyl or phenyl-$(C_1-C_4)$alkyl radicals mentioned being bonded to the pyridone ring directly or via a methylene or ethylene group, and $R^2$ is a hydrogen atom, an alkyl having 1 to 6 carbon atoms, an alkenyl having 2 to 6 carbon atoms or a benzyl radical, the alkyl, alkenyl or benzyl radicals being unsubstituted or substituted in the manner described for $R^1$.

Among the radicals $R^1$ and $R^2$ which contain the phenyl radical, those in which this phenyl nucleus is unsubstituted or only mono- or disubstituted are preferred. Preferred radicals among those mentioned for $R^2$ are alkyl radicals having 1 to 4, in particular 1 to 2 carbon atoms, and preferred radicals among the alkenyl radicals are those having 2, 3 or 4 carbon atoms.

A compound of the formula I in which $R^1$ is 2,4,4-trimethylpentyl, cyclohexyl or 4-(4-chlorophenoxy)-phenoxymethyl and $R^2$ is methyl is especially preferably prepared.

The term halogen radical is understood as meaning a fluorine, chlorine, bromine or iodine atom. Alkyl means radicals which are derived, for example, from methane, ethane, propane, butane, pentane, hexane or heptane. The term alkenyl is understood as meaning radicals which are derived, for example, from ethene, propene, butene, pentene, hexene or heptene.

Examples of an organic acid or a salt thereof which is employed in the process according to the invention are valeric acid, phenoxyacetic acid, diphenylacetic acid, 4-n-pentylbenzoic acid, 2-methoxybenzoic acid, acetic acid, terephthalic acid, 4-dimethylaminobenzoic acid, 3-toluic acid, 3,4-dimethoxybenzoic acid, 3-butoxybenzoic acid, 2-chlorobenzoic acid, 4-n-heptylbenzoic acid, 4-toluic acid, 2,3-dimethylbenzoic acid, benzoic acid, salicylic acid, naphthoic acid, 2-toluic acid, 2,4,6-trimethylbenzoic acid, 3-methoxybenzoic acid, 4-t-butylbenzoic acid, 2,5-dimethylbenzoic acid, 4-n-butylbenzoic acid, trifluoroacetic acid or ion exchangers. Preferred organic acids are, for example, benzoic acid, 4-tertbutylbenzoic acid and/or trifluoroacetic acid. The sodium salt or potassium salt are advantageously employed as the salts. 0.1 to 40 percent by weight of the organic acid, with respect to the pyrone of the formula II, are employed, preferably 5 to 20 percent by weight, in particular 8 to 12 percent by weight.

The hydroxylammonium salt is employed in the equimolar amount with respect to the pyrone of the formula II; however, it can also be employed in excess in order to accelerate the reaction, better yields often then being obtained. It may also be expedient to add the hydroxylammonium salt in several portions in the course of the reaction. All salts of hydroxylamine, for example the chloride, the sulfate or the acetate, can essentially be used as the hydroxylammonium salt. However, it is preferable to carry out the reaction with the readily accessible hydroxylammonium sulfate or chloride.

An alkali metal carbonate or alkali metal bicarbonate are preferably employed as the basic compounds in the process according to the invention in an amount of 0.8 to 5 equivalents with respect to the hydroxylammonium salt, in particular 0.9 to 1.1 equivalents.

Possible alkali metal carbonates or alkali metal bicarbonates are virtually all the carbonates and bicarbonates of the alkali metals, for example $Li_2CO_3$, $Na_2CO_3$, $K_2CO_3$, $NaHCO_3$ and $KHCO_3$. The carbonates and bicarbonates of sodium and of potassium are preferred, and $Na_2CO_3$ is particularly preferred. The alkali metal carbonates and alkali metal bicarbonates can be employed either individually or in practically any mixture. Their amount is expediently at least equivalent to the amount of hydroxylammonium salt used, but if an excess of hydroxylammonium salt is used, a smaller amount of alkali metal carbonate or alkali metal bicarbonate can also be employed. For example, 0.5 mol of $Na_2CO_3$ or 1 mol of $NaHCO_3$ is to be used per mole of hydroxylammonium chloride.

To carry out the process according to the invention, the pyrone of the formula II is advantageously mixed with the hydroxylammonium salt, the alkali metal carbonate and the organic acid, and the resulting crystal slurry is heated until no pyrone of the formula II can be detected; after the inorganic salts and the organic acid has been removed, the pyridone of the formula I formed is isolated directly or, even better, as the salt of an organic base, for example as the ethanolamine salt. The process according to the invention is carried out at a temperature of 50° C. to 120° C., preferably 60° C. to 105° C.

The organic acid is removed from the reaction batch by distillation or neutralization with subsequent filtration or extraction. Working up is carried out, for example in the case of benzoic acid, by dissolving the batch in ethyl acetate and washing the solution with bicarbonate solution or with sodium hydroxide solution. If washing is carried out with sodium hydroxide solution, it must be ensured that the aqueous phase is sufficiently dilute, and that a pH of about 8.0 is not exceeded, since otherwise emulsion effects occur, which cause poor phase separation. The treatment with the base can also be carried out by adding a little more solid $NaCO_3$ to the batch after the reaction has ended and subsequently stirring the batch. Benzoic acid and the acid impurities form sodium salts by this procedure. The largest proportion of the salts obtained can be removed by filtration with suction, and the remainder can be removed by washing the organic phase with water.

Trifluoroacetic acid can also be partly removed from the reaction batch by distillation under reduced pressure.

Solvents are added in small amounts or in an amount of up to 50 percent by weight of the total reaction batch. The amount is preferably 3 to 15 percent by weight. The solvents can be polar or non-polar and water-miscible or -immiscible. The following substances, for example, can be used:

water, low molecular weight alcohols, such as methanol, ethanol or isopropanol, ethylene glycol, ethylene glycol monomethyl ether, propylene glycol, acid amides, such as dimethylformamide, and esters, such as ethyl acetate, ethers, such as diisopropyl ether, chlorinated hydrocarbons, such as chlorobenzene, nitriles, such as acetonitrile, and hydrocarbons of an aliphatic, cycloaliphatic or aromatic nature, such as heptane or toluene.

The yields of the compound of the formula I achieved are as a rule 60% to 77%, based on the pyrone of the formula II, depending on the organic acid used.

Compared with the process in DE 36 26 210, the process according to the invention is distinguished by higher yields and by higher profitability.

EXAMPLES 1 to 26

4-Methyl-6-(2,4,4-trimethylpentyl)-2-pyrone, hydroxylammonium chloride, sodium carbonate and in each case 5 percent by weight of the organic acids mentioned in Table 1 are suspended in 200 ml of heptane and 2 ml of water. The reaction mixture is heated at 95° C. under reflux conditions for 12 hours. The yields with and without the addition of an organic acid are stated in Table 1. The yield of 1-hydroxy-4-methyl-6-(2,4,4-tri-methylpentyl)-2-pyridone is determined by sampling from the reaction batch and subsequent determination by high pressure liquid chromatography (HPLC). The yield is based on the pyrone employed.

TABLE 1

| Example No. | Addition | Yield [%] |
|---|---|---|
| 0 | no addition | 58 |
| 1 | valeric acid | 61 |
| 2 | phenoxyacetic acid | 61 |
| 3 | diphenylacetic acid | 62 |
| 4 | 4-n-pentylbenzoic acid | 63 |
| 5 | 2-methoxybenzoic acid | 63 |
| 6 | acetic acid | 64 |
| 7 | terephthalic acid | 64 |
| 8 | 4-dimethylamino-benzoic acid | 64 |
| 9 | 3-toluic acid | 64 |
| 10 | 3,4-dimethoxybenzoic acid | 64 |
| 11 | 3-butoxybenzoic acid | 65 |
| 12 | 2-chlorobenzoic acid | 66 |
| 13 | 4-n-heptylbenzoic acid | 66 |
| 14 | 4-toluic acid | 67 |
| 15 | 2,3-dimethylbenzoic acid | 67 |
| 16 | benzoic acid | 68 |
| 17 | salicylic acid | 68 |
| 18 | naphthoic acid | 68 |
| 19 | 2-toluic acid | 68 |
| 20 | 2,4,6-trimethylbenzoic acid | 68 |
| 21 | 3-methoxybenzoic acid | 68 |
| 22 | trifluoroacetic acid | 68 |
| 23 | 2,5-dimethylbenzoic acid | 70 |
| 24 | 4-n-butylbenzoic acid | 70 |
| 25 | 4-t-butylbenzoic acid | 70 |
| 26 | benzoic acid sodium salt | 66 |

The HPLC determination is carried out under the following conditions:

Column: diol column (E. Merck, Darmstadt, FRG) 7 μm 250 mm/4 mm

Element: acetonitrile with 6 ml of 85% strength $H_3PO_4$ per liter

Flow: 2 ml/minute

Detector: UV 198 mm (with a band width of 10 mm) 284 mm (with a band width of 4 mm)

EXAMPLE 27

4-Methyl-6- (2,4,4-trimethylpentyl) -2-pyrone is reacted as in Example 1 with different amounts of benzoic acid, in each case with respect to the starting substances. Table 2 shows the results.

TABLE 2

| Percentages by weight of benzoic acid | Yield [%] |
|---|---|
| 3 | 68.4 |
| 5 | 68 |
| 7 | 69.4 |
| 9 | 70 |

TABLE 2-continued

| Percentages by weight of benzoic acid | Yield [%] |
|---|---|
| 13 | 71 |
| 20 | 72.3 |
| 30 | 71.8 |
| 40 | 70.8 |

The determination is carried out by HPLC measurement from the reaction solution.

EXAMPLE 28

The reaction is carried out as in Example 1 with different amounts of 4-t-butylbenzoic acid, in each case with respect to the starting substance. Table 3 shows the results.

| Percentages by weight of 4-t-butylbenzoic acid | Yield [%] |
|---|---|
| 5 | 70 |
| 10 | 73.1 |
| 20 | 76.9 |
| 30 | 71.8 |

The determination is carried out by HPLC measurement from the reaction solution.

EXAMPLE 29

222.3 g (1 mol) of 4-methyl-6-(2,4,4-trimethylpentyl)-2-pyrone, 195.8 g (2.84 mol) of hydroxylammonium chloride, 149.2 g (1.41 mol) of Na$_2$CO$_3$, 21.9 g (0.18 mol) of benzoic acid and 2 ml of H$_2$O and 200 ml of heptane are combined and boiled under reflux for 12 hours. 21.9 g of Na$_2$CO$_3$ (0.207 mol) are then carefully added in portions and the mixture is boiled under reflux for a further hour. The mixture is filtered while still hot and the salts are washed with ethyl acetate (EtOAc). The organic phase is evaporated and the residue is taken up in 1000 ml of EtOAc, the mixture is washed three times with 1000 ml of water each time and the aqueous phases are extracted once with 300 ml of EtOAc. After the combined organic phases have been dried over Na$_2$SO$_4$ they are evaporated to about 600 ml and the 1-hydroxy-4-methyl-6-(2,4,4-trimethylpentyl)-2-pyridone is precipitated by addition of 49 ml of ethanolamine. Before being filtered off with suction, the precipitate is cooled to 5°–10° C. overnight in a refrigerator.

Yield: 175–178 g (65.2 to 66.3%) Melting point: 124° C.

EXAMPLE 30

204.2 g (0.9 mol) of 4-methyl-6-(2,4,4-trimethylpentyl)-2-pyrone (98%), 179.4 g (2.56 mol) of hydroxylammonium chloride (99%) and 135.9 g (1.27 mol) of sodium carbonate (99%) are suspended in 200 ml of n-heptane and 2 ml of water, and 12.6 ml (0.16 mol) of trifluoroacetic acid are added. During this addition, severe evolution of CO$_2$ occurs. The reaction mixture is heated at 95° C. for 15 hours, while stirring. The mixture is allowed to cool and is extracted with 300 ml of 0.1N NaOH. Heptane and the trifluoroacetic acid which remains are distilled off under reduced pressure, the residue is dissolved in 400 ml of ethyl acetate, and 48.6 g (0.79 mol) of ethanolamine are added to the resulting solution at about 50° C. After seeding, the solution is allowed to cool. The crystals formed are filtered off with suction, washed with a little cold ethyl acetate and dried. The yield of 1-hydroxy-4-methyl-6-(2,4,4-trimethylpentyl)-2-pyridone (ethanolamine salt) is 169.3 g (63%).

We claim:

1. A process for the preparation of a 1-hydroxy-2-pyridone of the formula I

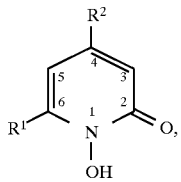

by reaction of a pyrone of the formula II

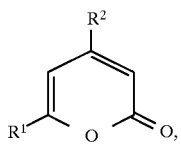

with a hydroxylammonium salt which comprises carrying out the reaction in the presence of an organic acid or a salt thereof in an amount of from 0.1 to 40 percent by weight with respect to the pyrone of formula II wherein said organic acid or salt thereof is selected from the group consisting of valeric acid, phenoxyacetic acid, diphenylacetic acid, 4-n-pentylbenzoic acid, 2-methoxybenzoic acid, terephthalic acid, 4-dimethylamino-benzoic acid, 3-toluic acid, 3,4-dimethoxybenzoic acid, 3-butoxybenzoic acid, 2-chlorobenzoic acid, 4-n-heptylbenzoic acid, 4-toluic acid, 2,3-dimethylbenzoic acid, benzoic acid, salicylic acid, naphthoic acid, 2-toluic acid, 2,4,6-trimethylbenzoic acid, 3-methoxybenzoic acid, trifluoroacetic acid, 2,5-dimethylbenzoic acid, 4-n-butylbenzoic acid, 4-t-butylbenzoic acid and benzoic acid sodium salt and a basic compound selected from an alkali metal carbonate or an alkali metal bicarbonate in an amount of 0.9 to 1.1 equivalents with respect to the hydroxylammonium salt, the radicals R$^1$ and R$^2$ in the formulae I and II having the following meanings:

R$^1$ is a branched or unbranched alkyl having 1 to 17 carbon atoms, a branched or unbranched alkenyl having 2 to 17 carbon atoms, a cycloalkyl having 3 to 8 carbon atoms in the ring, the cycloalkyl radical mentioned being unsubstituted or substituted by 1 to 3 alkyl radicals each having 1 to 3 carbon atoms, a phenyl, phenyloxy-(C$_1$–C$_4$)alkyl or phenyl-(C$_1$–C$_4$)alkyl radical which is unsubstituted or substituted in the aromatic nucleus by 1 to 3 (C$_1$–C$_6$)-alkyl, benzyl, (C$_1$–C$_6$) alkoxy, phenoxy or halogen radicals, it also being possible for the benzyl or phenoxy group present as a substituent to be substituted in the same manner, and the cycloalkyl, phenyl, phenyloxy-(C$_1$–C$_4$)alkyl or phenyl-(C$_1$–C$_4$)alkyl radicals mentioned being bonded to the pyridone ring directly or via a methylene or ethylene group, and R$^2$ is a hydrogen atom, an alkyl having from 1 to 6 carbon atoms, an alkenyl having 2 to 6 carbon atoms or a benzyl radical, the alkyl, alkenyl or benzyl radicals being unsubstituted or substituted in the manner described for R$^1$.

2. The process as claimed in claim 1, wherein a compound of the formula I is prepared in which R$^1$ is alkyl having 1 to 10 carbon atoms, cyclohexyl or phenoxymethyl and R$^2$ is (C$_1$–C$_4$)alkyl, or the radicals R$^1$ or R$^2$, which contain the phenyl nucleus, are unsubstituted or carry not more than 2 substituents.

3. The process as claimed in claim 1, wherein a compound of the formula I is prepared in which $R^1$ is 2,4,4-trimethylpentyl, cyclohexyl or 4-(4-chlorophenoxy)-phenoxymethyl and $R^2$ is methyl.

4. The process as claimed in claim 1, wherein said basic compound is selected from the group consisting of sodium carbonate, potassium carbonate, sodium bicarbonate, or potassium bicarbonate and hydroxylammonium chloride is employed as the hydroxylammonium salt.

5. The process as claimed in claim 1, which is carried out at a temperature of 50° C. to 120° C.

6. The process as claimed in claim 1, wherein a solvent is employed in an amount of up to 50 percent by weight of the total reaction batch.

7. The process as claimed in claim 6, wherein said solvent is selected from the group consisting of heptane or toluene.

8. The process as claimed in claim 1, which further comprises washing the reaction batch with a solution selected from a sodium carbonate or sodium hydroxide solution.

9. The process as claimed in claim 6 which further comprises removing by distillation reaction components selected from the solvent, the organic acid or both solvent and organic acid.

10. The process as claimed in claim 1 wherein said organic acid is present in an amount of 5 to 20 percent by weight with respect to the pyrone of the formula II.

11. The process as claimed in claim 1 wherein said organic acid or salt thereof is selected from the group consisting of benzoic acid, 2,5-dimethylbenzoic acid, 4-n-butylbenzoic acid and 4-t-butylbenzoic acid.

12. The process as claimed in claim 9 wherein said organic acid or salt thereof is selected from the group consisting of benzoic acid, 2,5-dimethylbenzoic acid, 4-n-butylbenzoic acid and 4-t-butylbenzoic acid.

13. The process as claimed in claim 12 wherein said organic acid or salt thereof is present in an amount from 5 to 20 percent by weight with respect to the pyrone of formula II.

14. The process as claimed in claim 1 wherein said organic acid or salt thereof is present in an amount from 8 to 12 percent by weight with respect to the pyrone of formula II.

15. The process as claimed in claim 13 wherein said organic acid or salt thereof is present in an amount from 8 to 12 percent by weight with respect to the pyrone of formula II.

16. The process as claimed in claim 1 wherein said 1-hydroxy-2-pyridone of formula I is obtained in at least 61% yield.

17. The process as claimed in claim 15 wherein said 1-hydroxy-2-pyridone of formula I is obtained in at least 61% yield.

* * * * *